United States Patent [19]

Dokus et al.

[11] 4,213,161
[45] Jul. 15, 1980

[54] MOTOR CONTROL FOR SLOW SPEED TAPE RECORDER

[75] Inventors: Edwin A. Dokus, Winchester; David Banks, South Hamilton, both of Mass.

[73] Assignee: American Optical Corporation, Southbridge, Mass.

[21] Appl. No.: 956,829

[22] Filed: Nov. 2, 1978

[51] Int. Cl.² .................. G11B 15/46; G11B 19/02
[52] U.S. Cl. ........................... 360/73; 360/90; 360/137
[58] Field of Search ............... 360/90, 73, 26–27, 360/51, 137; 318/311

[56] References Cited

U.S. PATENT DOCUMENTS

| | | | |
|---|---|---|---|
| Re. 29,921 | 2/1979 | Cherry et al. | 360/73 X |
| 3,347,997 | 10/1967 | Woodruff | 360/27 |
| 3,742,320 | 6/1973 | Ban | 300/73 |
| 3,913,869 | 10/1975 | Richards | 360/90 X |
| 3,982,277 | 9/1976 | Naylor | 360/27 |

*Primary Examiner*—John H. Wolff

*Attorney, Agent, or Firm*—Jeremiah J. Duggan; Stephen A. Schneeberger; Alan H. Spencer

[57] ABSTRACT

An improved control is provided for the tape transport motor of a battery-powered, slow-speed tape recorder typically used for producing magnetic recordings of an ambulatory patient. The recorder's tape transport means is driven by a synchronous AC motor powered from a DC (battery) supply. That DC supply, during normal operation, is voltage regulated to provide desired speed stability. That DC supply is inverted into a square wave DC current in a manner effectively providing a regulated square wave AC at twice the regulated DC voltage. Phase-shifting means connected to the inverter provide a phase-shifted square wave source necessary for the two-phase AC synchronous motor. In an improved mode of control, means are additionally provided for selectively supplying current at full battery voltage, square wave inverted and phase-shifted to the AC synchronous motor in lieu of the regulated supply voltage to provide high torque operation for selected periods of time as during "start-up" or "warm-up".

4 Claims, 2 Drawing Figures

MOTOR CONTROL FOR SLOW SPEED TAPE RECORDER

BACKGROUND OF THE INVENTION

This invention relates to slow speed tape recorders and in particular to those magnetic tape recorders which are utilized in the recording of physiological signals of a patient.

In conjunction with the examination of a patient to determine general cardiac conditions and the diagnosing of health problems relating thereto, electrical signals that circulate upon the surface of a person's skin as a result of expansions and contractions of the cardiac muscles are recorded on magnetic tape and subsequently analyzed by a cardiologist or other trained medical personnel. In the recording of such signals, a portable-type tape recorder may be used to obtain the continous ECG signals for a long period of time, such as 24 hours or so. In one device for this purpose, the Model 7007 Recorder supplied by the American Optical Corporation, the recording is done on a tape cassette somewhat similar to standard cassettes utilized in a portable tape recorder. In order to accomplish a recording for a period of such as 24 hours on a single "standard" tape cassette, the tape speed must be well below the conventional 1⅞ inches per second. Accordingly, the above-mentioned device utilized a tape speed of approximately 1/16 inch-per-second to achieve this long duration recording.

It should be recognized that it is very important that the tape speed be constant throughout the duration of the recording, so that when the tape is reviewed, the time intervals between the particular portions of the ECG signal which are of interest (e.g. the R-wave) that an accurate record is available. For instance, the distance between R-waves or the time interval therebetween indicating successive beats of the heart are often measured. It will be noted that these time intervals might vary greatly if the tape speed were not held constant during a recording and playback thereof. Thus, it is necessary to keep both the high frequency variation (flutter) and the low frequency variation (wow) to a minimum. As may be recognized, this can be exceedingly difficult in a miniature portable slow speed tape recorder.

The recorder of the above design, in order to accomplish the desired ends, utilizes a battery-powered drive including a synchronous AC motor. The power to the synchronous motor is provided by converting the constant DC current available from the battery to a square wave DC signal analogous to an AC signal. Additionally, this signal is divided and one portion thereof is phase-shifted so that a split-phase, or two-phase, current source is available to drive the corresponding phases of the AC synchronous motor.

An AC motor nominally rated at 300 rpm at 60 cycles AC at 12 volts and 0.75 oz/in. of torque has been found to be quite effective as a capstan drive in the portable tape recorder in the above-identified unit. The motor, it should be recognized, is not operated at rated conditions, however, being driven at 4 volts switched plus and minus at a frequency of 64 hertz. It should be recognized by those skilled in the art that 64 is a convenient multiple of conventional clocking devices. The motor has been found to have sufficient torque for the driving of the capstan and the related cassette to provide very stable tape operation, particularly when the unit is incorporated with such features as is described in U.S. Pat. Nos. 3,882,543; 3,913,869; and 3,982,277, all assigned to the assignee of the present application.

The drive mechanism illustrated in U.S. Pat. No. 3,913,869 particularly enables the motor of the present recorder to reach operating speed synchronously while picking up the load of the capstan and the cassette. This is accomplished through the clutch mechanism and the belt arrangement disclosed in the afore-mentioned patent which allows the synchronous motor sufficient revolution to develop the torque necessary to drive the related load. While this illustrated drag mechanism is sufficient to enable the synchronous recorder motor to reach operating speed and assume the load of the cassette under normal operating conditions, it is essential in the initial moments of operating such a physiological recorder that continuous synchronous operation be assured. During these initial first moments of operation of the recorder, calibrations are performed and the coded timing track of the ECG recording tape is initiated. In order to assure that the subsequent long duration 24-hour recording begins from a properly calibrated base, rated speed operation of the motor is essential. In view of this desired high reliability of operation, further startup stabilization of the synchronous motor was felt important.

By providing special startup operating mode for the recorder, it is also further felt that economics in current usage under continued operation might be gained. It is well recognized that the maximum torque of a synchronous motor is achieved during the synchronous operation. Thus, the present invention, directed to assuring a fully synchronous operation of a battery-powered synchronous motor throughout the full operating range thereof (including startup) promotes efficient use of the battery power. Particularly, we have determined that a special operating mode for the first few moments of recorder operation additionally enhances the calibration of the tape operation and thus expedites the application of the recorder to patient ECG signal monitoring.

These and further objectives of the present invention will be understood from the following description of the invention.

SUMMARY OF THE INVENTION

Among the several features of the improvement disclosed herein of a battery-powered, slow-speed tape recorder for producing magnetic recordings of physiological information of an ambulatory patient are a self-contained portable tape recorder capable of operating for a long period of time, such as 24 hours or more, at a very stable slow speed. The tape recorder includes tape transport means having a capstan-type tape drive and a take-up reel. The capstan drive, at least, is driven by a synchronous AC motor operatively coupled thereto. The synchronous motor is powered through DC supply, such as a battery, which during normal operation is voltage regulated to provide the desired speed stability. This DC supply is inverted through inverter means into a square wave DC current being modulated at essentially rated voltage plus and minus from the common terminal or common voltage of the battery supply. Such inverter means, thus, effectively, provides a regulated square wave AC at twice the regulated DC voltage.

Also included are phase-shifting means connected to the inverter drive to provide a phase-shifted square wave source necessary for the two-phase AC synchronous motor. The improvement also includes means to drive said AC synchronous motor from a square wave, plus-minus switched and phase-shifted signal coming directly from the battery, (or at full battery voltage) in lieu of the regulated supply voltage. Such selective application of the "full battery voltage" to the motor provides a high torque operation for selected periods of time as during a "warm-up" and thus allowing a lower voltage operation during physiological recording and thus more economical usage of the available battery power.

DESCRIPTION OF A PREFERRED EMBODIMENT

Figure 1:
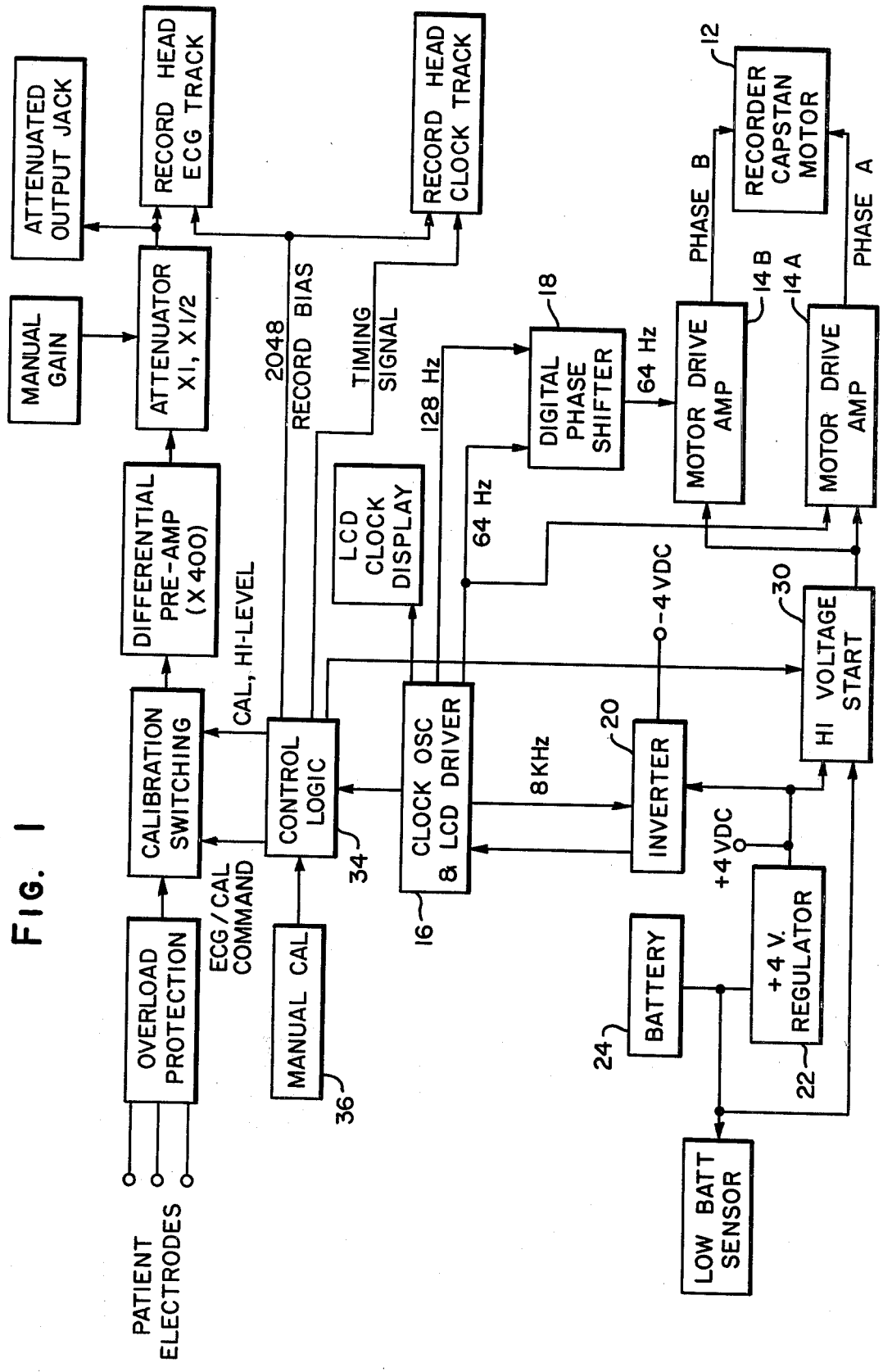
FIG. 1 is a diagrammatic illustration of the invention in block diagram form.

Referring now to the drawings and FIG. 1 in particular, the relationship of the present invention to the function of a physiological signal recorder can be seen. Motor 12 receives its driving current from motor drive amplifier 14 which receives a 64 hertz signal from oscillator 16. As may be seen, a phase shifter (digital) 18 is intermediate the control 16 and driver 14 to provide also a phase-shifted signal for the "two phase" AC synchronous motor 12. Oscillator 16 is powered by inverter 20 which is supplied directly from voltage regulator 22 to supply B⁻ to the various electronic components in the recorder. Motor drive amplifier 14 has duplicate sections 14A and 14B to power the A and B windings of the synchronous motor 12. In the embodiment subsequently described, motor drive amplifiers 14A and 14B each alternately reverse the power to the motor windings as triggered by the 64 hertz signal from oscillator 16 such that motor 12 sees alternately "plus" four volts and "minus" four volts, or effectively, 64 hertz, 8 volt AC power.

Starter circuit 30 is disposed to directly supply full battery supply (6 volts) to motor 12 through drivers 14A and 14B. As before, when signaled by control logic 34, oscillator 16 and driver 14B and phase-shifter 18, provide "split-phase" power to motor 12 to satisfy the multi-phase requirements of the AC synchronous motor 12 during this 12-volt operation.

Starter circuit 30 receives its command from control logic circuit 34. In the illustrated embodiment, motor 12 is powered through the starter circuit 30 during the recorder calibration function. Thus, when the manual calibration circuit 36 is operative, control logic circuit 34 senses this condition and powers motor 12 directly from battery 24.

Again, in the preferred embodiment of physiological recorder illustrated, recorder operation is conventionally started with a calibration function. In this regard, these functions (start and calibration) are simultaneous. One skilled in the art should recognize that such simultaneous operation is not necessary and could easily be made independent, as by the starter 30 being activated for a predetermined period of time as by a latching relay through a "power on" switch, after which regulated 4 volt operation might be continued.

Figure 2:
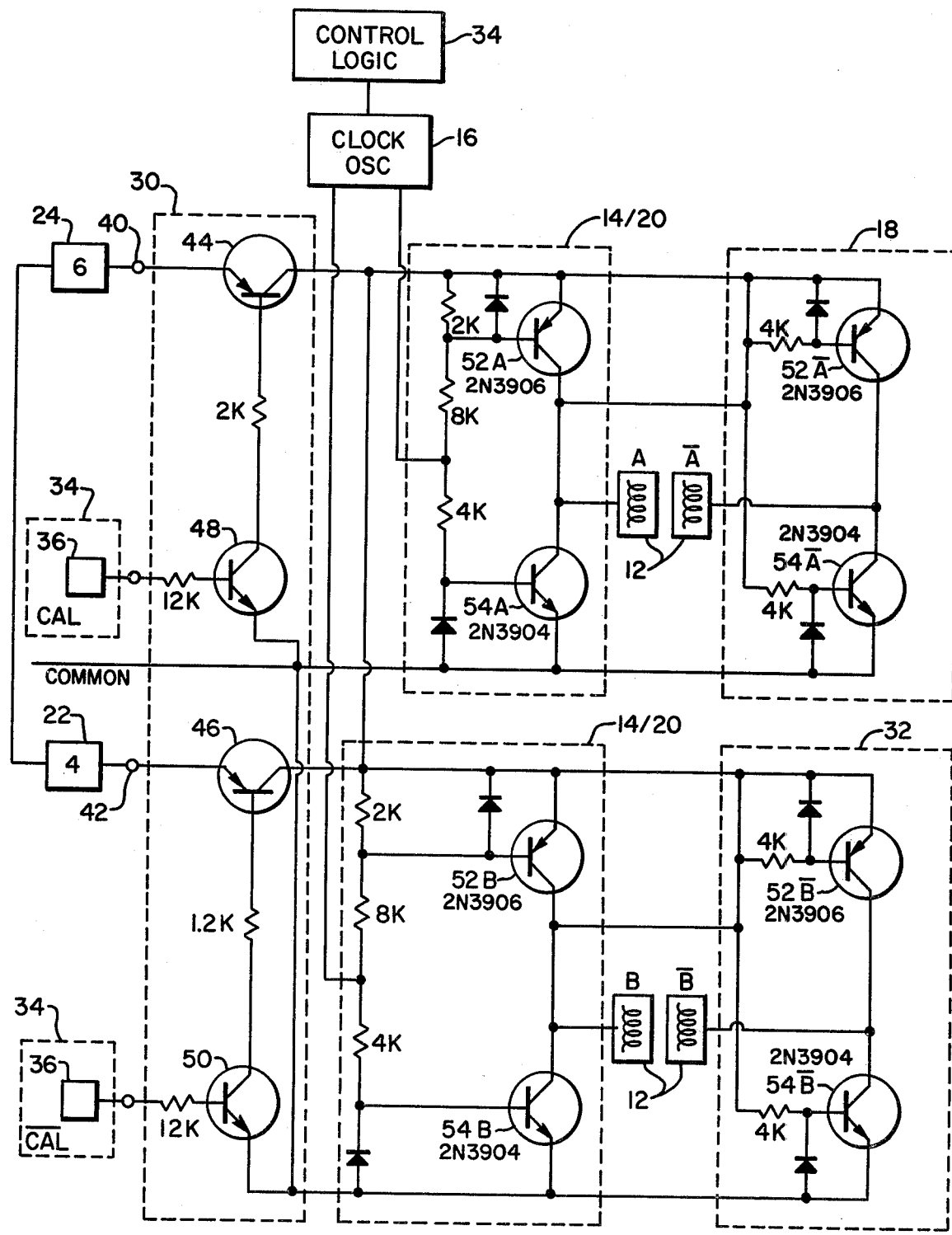
FIG. 2 is an electrical schematic illustrating certain features of the invention.

In the illustrated embodiment of recorder, the start circuit 30 is implemented as further illustrated in FIG. 2, wherein reference numbers of elements common to those of FIG. 1 are the same. As illustrated, battery system 24 supplies start circuit 30 at terminal 40 and at terminal 42 (through regulator 22). Switches 44 and 46 control the application of direct battery voltage (6 v.) as regulated voltage (4 v.) to the driver/inverter 14/20 functions of the overall motor 12 supply. Switches 44 and 46 are reciprocally connected such that when the manual calibration function is selected, directly battery voltage is input at terminal 44. When the "ECG record" function is selected, (the antithesis of "calibrate") regulated voltage is supplied at terminal 46. These functions of switches 44 and 46 are accomplished through switches 48 and 50 which provide through the inputs from calibration control 36 and control logic 34 circuits the requisite base current for operation of the transistor switches. As may be seen, with the appropriate supply to terminals 44 or 46, inverter switches 52 and 54 (A, $\overline{A}$, B, and $\overline{B}$) provide alternately plus and minus system voltage to the respective windings A, $\overline{A}$, B, $\overline{B}$ of motor 12. In the illustrated embodiment, the phase-shifted power is provided by the delayed sequencing of switches 52A, 54$\overline{A}$, 52B, and 54$\overline{B}$, such that motor windings 12$\overline{A}$ and 12$\overline{B}$ are properly sequentially powered.

In the illustrated embodiments, switches 44, 46, and 52 are 2 N 3906 transistors and switches 48, 50 and 54 are 2 N 3904 transistors, appropriately biased by the resistance and diodes illustrated in FIG. 2. The illustrated diodes are 1 N 914.

Although the invention has been described with reference to the embodiment of a physiological recorder, it is to be understood that this embodiment is merely illustrative of the application of a low-power AC synchronous motor optimized for efficient assured synchronous operation. Numerous modifications may be made therein and other arrangements of the power sequencing may be devised without departing from the spirit and scope of the invention.

We claim:

1. In a battery-powered slow-speed tape recorder for recording physiological information of an ambulatory patient, said recorder including tape transport means including a capstan tape drive and a take-up reel drive, a synchronous AC motor operatively coupled to at least said capstan, and battery means for supplying DC current to power said motor, an improved motor control comprising:

voltage regulating means for supplying current from said battery at a predetermined regulated voltage less than full battery voltage;

inverter means connected to said regulator means for converting DC current to a square wave DC current of predetermined frequency, said square wave being modulated to regulated voltage plus and minus about the common of said battery voltage;

phase-shifting means connected to said inverter means to supply a phase-shifted square wave DC current at said predetermined frequency;

means connecting said square wave DC and said phase-shifted square wave DC to said AC synchronous motor; and means for selectively supplying current at full battery voltage, square wave inverted and phase-shifted, to said AC synchronous motor in lieu of said regulated supply voltage whereby to afford synchronous operation of said motor throughout the full operating interval of the recorder.

2. The recorder according to claim 1 wherein said recorder includes means for calibrating the recording function including means to selectively supply to said synchronous motor said current at full battery voltage concurrent with at least a portion of said calibrating function.

3. The recorder according to claim 1 wherein said recorder includes means to selectively apply said current at full battery voltage for a predetermined start-up time as a function of powering up said recorder.

4. The recorder according to claim 1 where said means for selectively supplying current at full battery voltage (square wave-inverted and phase-shifted) to said AC synchronous motor includes inverter means and phase-shift means independent of said inverter and phase-shift means for said regulated voltage supply.

* * * * *